United States Patent [19]

Mosbach et al.

[11] Patent Number: 5,098,983
[45] Date of Patent: Mar. 24, 1992

[54] POLYISOCYANATE MIXTURES, PROCESSES FOR THEIR PRODUCTION AND THEIR USE AS BINDERS FOR COATING COMPOSITIONS OR AS REACTANTS FOR COMPOUNDS REACTIVE TO ISOCYANATE GROUPS OR CARBOXYL GROUPS

[75] Inventors: Jürgen Mosbach, Bergisch Gladbach; Hans-Josef Laas, Cologne; Werner Kubitza, Leverkusen, all of Fed. Rep. of Germany

[73] Assignee: Bayer Aktiengesellschaft, Leverkusen, Fed. Rep. of Germany

[21] Appl. No.: 644,798

[22] Filed: Jan. 23, 1991

[30] Foreign Application Priority Data

Jan. 23, 1990 [DE] Fed. Rep. of Germany ....... 4001783

[51] Int. Cl.⁵ .............................................. C08G 18/34
[52] U.S. Cl. ........................................ 528/59; 528/60; 528/61; 528/65; 528/73; 252/182.21; 252/182.22
[58] Field of Search ............... 528/59, 60, 61, 65, 528/73; 252/182.21, 182.22

[56] References Cited

U.S. PATENT DOCUMENTS

| | | | |
|---|---|---|---|
| 3,412,054 | 11/1968 | Milligan et al. | 260/18 |
| 3,959,348 | 5/1976 | Reiff et al. | 260/471 |
| 4,184,989 | 1/1980 | Flakus et al. | 260/29.2 |
| 4,476,054 | 10/1984 | Disteldorf et al. | 260/239 |
| 4,496,684 | 1/1985 | O'Connor et al. | 524/591 |
| 4,801,623 | 1/1989 | Hess et al. | 521/157 |
| 4,929,724 | 5/1990 | Engbert et al. | 540/202 |

FOREIGN PATENT DOCUMENTS 1153815 5/1969 United Kingdom .

Primary Examiner—Maurice J. Welsh
Attorney, Agent, or Firm—Joseph C. Gil; Thomas W. Roy

[57] ABSTRACT

The present invention relates to polyisocyanate mixtures having
  a) an average NCO functionality of 1.5 to 4.0,
  b) a content of (cyclo)aliphatically bound isocyanate groups (calculated as NCO, MW 42) of 2 to 40% by weight,
  c) a content of chemically incorporated carboxyl groups (calculated as COOH, MW 45) of 0.01 to 15% by weight and
  d) a content of (cyclo)aliphatically bound uretdione groups (calculated as $C_2N_2O_2$, MW 84) of 1 to 23% by weight.

The present invention also relates to processes for the production of these polyisocyanate mixtures and to their use, optionally after at least partial neutralization with tertiary amines, as binders for coating compositions which may be crosslinked under the effect of moisture and/or heat and as reactants for compounds containing isocyanate- and/or carboxyl-reactive groups in the production of high molecular weight plastics.

8 Claims, No Drawings

POLYISOCYANATE MIXTURES, PROCESSES FOR THEIR PRODUCTION AND THEIR USE AS BINDERS FOR COATING COMPOSITIONS OR AS REACTANTS FOR COMPOUNDS REACTIVE TO ISOCYANATE GROUPS OR CARBOXYL GROUPS

BACKGROUND OF THE INVENTION

1. Field of the Invention

This invention relates to new polyisocyanate mixtures which contain both carboxyl groups and aliphatically and/or cycloaliphatically bound uretdione groups, to processes for the production of these polyisocyanate mixtures and to their use as binders for coating compositions or as reactants for isocyanate-reactive compounds in the production of high molecular weight plastics. 2. Description of the Prior Art Polyisocyanates which contain uretdione groups and are free from masking agents are heat-activatable, crosslinking agents for intermediate products containing isocyanate-reactive groups for the production of plastics. These polyisocyanates are interesting because they are capable of reacting with compounds containing isocyanate-reactive groups both at room temperature (free NCO groups) and at relatively high temperatures (blocked NCO groups) in an addition reaction. Thus, allophanate groups are formed, for example, from hydroxyl groups and uretdione groups at elevated temperatures. Of industrial significance are inter alia compounds containing cycloaliphatically bound uretdione groups (DE-AS 3,030,513) or aliphatically bound uretdione groups (DE-OS 3,437,635).

Compounds containing isocyanate groups and free carboxyl groups are also known as intermediates for the production of plastics In the synthesis of aqueous polyurethane dispersions for example, NCO prepolymers having chemically incorporated carboxyl groups can be produced as intermediates through the use of sterically hindered hydroxyalkane carboxylic acids, such as dimethylol propionic acid, as disclosed in U.S. Pat. No. 3,412,054.

It has now surprisingly been found that the combination of these two principles, i.e., the simultaneous incorporation of (cyclo)aliphatically bound uretdione groups and carboxyl groups in modified polyisocyanate mixtures, results in a number of remarkable properties. Despite the simultaneous presence of isocyanate groups and carboxyl groups, the polyisocyanate mixtures according to the invention described in detail hereinafter remain stable in storage for at least three months at room temperature, are soluble or dispersible in water after neutralization with tertiary amines, crosslink spontaneously at elevated temperatures, demonstrate the property of being film-forming even in the absence of other auxiliaries and additives and are useful in various reactions with corresponding reactants by virtue of the simultaneous presence of three different reactive groups. In particular, they are suitable in combination with compounds containing isocyanate-reactive groups for the production of high molecular weight plastics.

SUMMARY OF THE INVENTION

The present invention relates to polyisocyanate mixtures having a) an average NCO functionality of 1.5 to 4.0, b) a content of (cyclo)aliphatically bound isocyanate groups (calculated as NCO, MW 42) of 2 to 40% by weight, c) a content of chemically incorporated carboxyl groups (calculated as COOH, MW 45) of 0.01 to 15% by weight and d) a content of (cyclo)aliphatically bound uretdione groups (calculated as $C_2N_2O_2$, MW 84) of 1 to 23% by weight.

The present invention also relates to a first process for the production of these polyisocyanate mixtures which comprises reacting A) a polyisocyanate component containing at least one polyisocyanate having (cyclo)aliphatically bound isocyanate groups, (cyclo)aliphatically bound uretdione groups and a molecular weight of 168 to 1,000 with B) a hydroxycarboxylic acid component comprising at least one aliphatic hydroxycarboxylic acid having a molecular weight of 76 to 200.

while maintaining an equivalent ratio of isocyanate groups hydroxyl groups of 1.05:1 to 80:1 during the reaction, and optionally distilling off any volatile, unreacted, starting polyisocyanate.

The present invention further relates to a second process for the production of these polyisocyanate mixtures which comprises i) reacting A) a polyisocyanate component which is essentially free from uretdione groups and contains at least one polyisocyanate having (cyclo)aliphatically bound isocyanate groups and a molecular weight of 168 to 1,000 with B) a hydroxycarboxylic acid component comprising at least one aliphatic hydroxycarboxylic acid having a molecular weight of 76 to 200, while maintaining an equivalent ratio of isocyanate groups to hydroxyl groups of 1.05:1 to 400:1 during the reaction, ii) subsequently dimerizing and optionally trimerizing 5 to 60% by weight of the isocyanate groups of the product obtained in i) in the presence of a dimerization catalyst and iii) optionally distilling off any volatile, unreacted, starting polyisocyanate.

The present invention finally relates to the use of the polyisocyanate mixtures, optionally after at least partial neutralization with tertiary amines, as binders for coating compositions which may be crosslinked under the effect of moisture and/or heat and as reactants for compounds containing isocyanate- and/or carboxyl-reactive groups in the production of high molecular weight plastics.

DETAILED DESCRIPTION OF THE INVENTION

In accordance with the present invention the term "(cyclo)aliphatic" means aliphatic and/or cycloaliphatic.

The polyisocyanate component A) to be used in the first process according to the invention contains at least one polyisocyanate having (cyclo)aliphatically bound isocyanate groups, a molecular weight of 168 to 1,000 and an NCO functionality of 2 to 4, preferably 2 to 3. Suitable polyisocyanates include monomeric organic diisocyanates (such as 1,6-diisocyanatohexane (HDI), 1-isocyanato-3,5,5-trimethyl-5-isocyanatomethyl cyclohexane (IPDI), 4,4'-diisocyanatodicyclohexyl methane)

and also modification products of these monomeric diisocyanates such as oxadiazinetrione polyisocyanates prepared from 2 moles of a monomeric diisocyanate, preferably 2 moles of HDI, with 1 mole of carbon dioxide; biuret polyisocyanates, preferably N,N',N"-tris-(isocyanatohexyl)-biuret and mixtures thereof with its higher homologs; isocyanurate polyisocyanates based on the monomeric diisocyanates previously set forth, preferably HDI and/or IPDI; uretdione diisocyanates such as dimeric HDI or dimeric IPDI; and mixtures of these polyisocyanates which meet the requirements stated above. The polyisocyanates to be used in the second process according to the invention are the same as those previously set forth, except that they do not contain uretdione groups.

The hydroxycarboxylic acid component B) to be used in both processes according to the invention contains at least one aliphatic hydroxycarboxylic acid having a molecular weight of 76 to 200, such as 2-hydroxyacetic acid, 4-hydroxybutyric acid, 2,2-bis-(hydroxymethyl)-propionic acid (DMPA). DMPA is particularly preferred for use as hydroxycarboxylic acid component B).

Other synthesis components containing aliphatically bound hydroxyl groups may optionally be used as further reactants in the processes according to the invention. These compounds are preferably nonionic hydrophilic synthesis components which provide hydrophilicity to the polyisocyanate mixtures according to the invention. Diols containing hydrophilic side chains of the type mentioned in U.S. Pat. No. 4,190,566 (herein incorporated by reference) or hydrophilic monohydric polyether alcohols of the type mentioned in U.S. Pat. No. 4,237,264 (herein incorporated by reference) are mentioned by way of example in this regard. Other compounds containing aliphatically bound hydroxyl groups which may optionally be used include low molecular weight chain extending agents or crosslinking agents, preferably having a maximum molecular weight of 200, such as ethylene glycol, propylene glycol, trimethylol propane or mixtures of such low molecular weight polyhydroxyl compounds. Chemically incorporated emulsifiers such as ethoxylated alkylphenols, preferably ethoxylated nonylphenols; and chemically incorporated emulsifiers containing ether or ester groups such as polyoxyethylene lauryl ethers or polyoxyethylene esters of higher fatty acids (e.g., polyoxyethylene laurate, oleate or stearate) may also be used as a further synthesis component containing an aliphatic hydroxyl group. These emulsifiers generally contain 8 to 50 oxyethylene units per molecule.

The previously mentioned compounds containing alcoholic hydroxyl groups may be used in quantities of up to 10% by weight, based on the weight of components A) and B), in the processes according to the invention.

In the first process according to the invention an equivalent ratio of isocyanate groups to hydroxyl groups of 1.05:1 to 80:1, preferably 1.2:1 to 50:1, is generally maintained during the production of the polyisocyanate mixtures, which is carried out at 20° to 100° C., preferably 25° to 90° C. reaction may be carried out either in the absence of solvents or in the presence of suitable solvents inert to isocyanate groups.

After either of the processes according to the invention, the reaction products may optionally be mixed with other organic polyisocyanates C) which include uretdione polyisocyanates containing aliphatically bound uretdione groups mentioned as suitable for use as component A) in accordance with the first process according to the invention. Other examples include aromatic uretdione diisocyanates such as dimerized or trimerized 2,4-diisocyanatotoluene or other polyisocyanates which are known from polyurethane chemistry such as those previously mentioned as suitable for use as starting component A) for either of the processes according to the invention.

In the second process according to the invention, as already mentioned, the starting polyisocyanates A) are essentially free of uretdione groups. These starting polyisocyanates are reacted with the previously described hydroxy carboxylic acids and optionally the previously described additional compounds having aliphatically bound hydroxyl groups, while maintaining an NCO/OH equivalent ratio of 1.05:1 to 400:1. This reaction is preferably done in the melt at 25° to 90° C.

In a second reaction stage, 5 to 60%, preferably 10 to 50%, of the isocyanate groups of the product from the first step are converted into uretdione groups and optionally isocyanurate groups in the presence of a catalyst that accelerates the dimerization of isocyanate groups such tri-n-butyl-or tri-n-octyl-phosphine. This means that in this oligomerization reaction up to 80%, preferably up to 50% of the isocyanate groups which react are converted into isocyanurate groups and the remainder into uretdione groups. Higher and/or mixed homologs of the respective oligomerization products may also be obtained. This oligomerization reaction is generally conducted at a temperature of 25° to 100°, preferably 25° to 90° C. The ratio of uretdione groups to isocyanurate groups in the oligomerization product can be controlled by suitably selecting the catalyst and particularly the reaction temperature.

The oligomerization reaction is terminated in known manner by the addition of a suitable catalyst poisons such as p-toluene sulfonic acid methylester or sulphur, or by removing the catalyst from the reaction mixture by distillation.

After the oligomerization reaction, the starting polyisocyanate A) that is still present may optionally be removed by, for example, flash distillation. In addition, the product may optionally be blended with other organic polyisocyanates C) as described hereinafter.

In accordance with both the first and second processes according to the present invention, the type of reactants, the quantities in which they are used, the amount of the starting polyisocyanate A) that is optionally removed at the end of the reaction, and the type and quantity of polyisocyanates C) which are optionally added are selected so that the resulting polyisocyanate mixtures according to the invention satisfy requirements a) to d) stated above. The particularly preferred polyisocyanate mixtures according to the invention have an average NCO functionality of 1.5 to 4, preferably 1.5 to 3; an NCO content of 2 to 40% by weight, preferably 5 to 20% by weight; a carboxyl group content of 0.01 to 15% by weight, preferably 0.5 to 5% by weight; and a content of aliphatically bound uretdione groups of 1 to 23% by weight, preferably 5 to 20% by weight.

By virtue of the simultaneous presence of three different reactive groups, the polyisocyanate mixtures according to the invention are valuable, versatile intermediate products or crosslinking agents for the production of high molecular weight plastics.

The polyisocyanate mixtures according to the invention may be converted into a water-dispersible or water-soluble form by partial or complete neutralization of the carboxyl groups with, for example, tertiary amines.

Tertiary amines suitable for this neutralization reaction include tertiary amines inert to isocyanate groups such as triethylamine, N-methyl pyrrolidine, N-methyl piperidine or N-methyl morpholine; and isocyanate-reactive tertiary amines, preferably amino alcohols, such as triethanolamine, N-methyl diethanolamine, 2-(N,N-dimethylamino)-isopropanol or N,N-dimethyl ethanolamine.

The at least partial neutralization of the carboxyl groups, followed by dissolution or dispersion of the polyisocyanate mixtures according to the invention in water, results in the formation of aqueous solutions or dispersions of self-crosslinking binders which, under the effect of water as a chain-extending agent, react to provide film-forming solutions or dispersions of high molecular weight plastics (cf. Example 1). In addition, the optionally at least partly neutralized polyisocyanate mixtures according to the invention are binders which crosslink spontaneously under the effect of moisture or heat and which show substantially indefinite storability at room temperature.

The polyisocyanate mixtures according to the invention may also be reacted with the relatively high molecular weight polyhydroxyl compounds known from polyurethane chemistry to form high molecular weight polyurethanes in which the uretdione groups or carboxyl groups are present as further reactive centers in addition to free isocyanate groups. These polyurethanes may undergo further reactions, preferably crosslinking reactions, with suitable reactants.

The polyisocyanate mixtures according to the invention may also be added as reactive emulsifiers to aqueous polymer dispersions to improve their property level.

When the carboxyl groups are at least partly converted into carboxylate groups, preferably by partial neutralization with tertiary amines, polyisocyanate mixtures according to the invention are formed which, by virtue of the presence of the basic centers, often have a desirable catalytic effect on the isocyanate addition reaction when used in accordance with the invention.

When the polyisocyanate mixtures according to the invention are used as paint binders or as additives for paints, the auxiliaries and additives known from paint technology may of course also be used. These auxiliaries and additives include pigments, fillers, solvents, flow control agents, plasticizers, etc.

In the following examples, all parts and percentages are by weight, unless otherwise stated.

EXAMPLES

EXAMPLE 1

1010.67 g of a polyisocyanate mixture having an NCO content of 21.6%, an average NCO functionality of 2.3 and a viscosity of 150 mPa · s/23° C., and containing a mixture of a uretdione diisocyanate and an isocyanurate polyisocyanate both of which were based on 1,6-diisocyanatohexane (HDI),
46.90 g dimethylol propionic acid (DMPA) and
30.6 g N-methyl morpholine (NMM)

were mixed while stirring and kept at 70° C. until the titrated NCO content of the reaction mixture had fallen to 15.3%.

After cooling to room temperature, a polyisocyanate mixture according to the invention was present partly in salt form.

| Characteristic data: | |
|---|---|
| viscosity (mPa · s/23° C.): | 1450 |
| Hazen color index: | 60 |
| uretdione groups (%) | 17.3 |
| carboxyl groups (%) | 1.2 |
| carboxylate groups (%) | 0.2 |

After application to a glass plate, the solution of the partially neutralized polyisocyanate mixture according to the invention dried after 2 hours at room temperature and after 30 minutes at 140° C. to form a clear, elastic, tear-free and tack-free film. The König pendulum hardness values were 40 sec for the film dried at room temperature and 70 sec for the heat-cured film.

For comparison a film of the starting polyisocyanate mixture applied to a glass plate remained liquid under the same drying conditions.

The stability in storage of the partly neutralized polyisocyanate mixture according to the invention was tested by titration of the NCO content and determination of viscosity as a function of the storage time at room temperature:

| Storage time (days) | NCO content (%) | Viscosity (mPa · s, 23° C.) |
|---|---|---|
| 0 | 15.3 | 1450 |
| 1 | 15.0 | 1460 |
| 5 | 14.9 | 1455 |
| 10 | 15.1 | 1450 |
| 30 | 14.8 | 1450 |
| 100 | 14.8 | 1450 |
| 150 | 14.6 | 1475 |

To prepare an aqueous dispersion, 550 g deionized water were added with vigorous stirring to 450 g of the partly neutralized polyisocyanate mixture according to the invention. A bluish, aqueous dispersion was formed and was stirred for 1 hour at room temperature until the evolution of gas was complete.

| Characteristic data: | |
|---|---|
| solids content: | 44% |
| average particle size of the dispersed solids: | 205 nm |
| viscosity (DIN 4 cup): | 20 sec |

The films of the aqueous polyurethane/urea dispersion dried at room temperature (a) and at 140° C. (b) were clear, crack-free and elastic. The König pendulum hardness values were 50 sec (a) and 80 sec (b).

100 g of the partly neutralized polyisocyanate mixture were introduced into a 2 liter Erlenmeyer flask and, after the addition of 30 g deionized water, were briefly stirred and left standing. An ascending porous foam mushroom formed in 1 minute with evolution of $CO_2$.

EXAMPLE 2

1010.67 g of the starting polyisocyanate mixture of Example 1,
167.5 g DMPA and

-continued 130 g N-methyl pyrrolidone (NMP were mixed and stirred at 80° C. until the titrated NCO content had fallen to 8.6%. After cooling to room temperature, a clear solution of a polyisocyanate mixture according to the invention in NMP was obtained.

| Characteristic data: | |
|---|---|
| solids content (%): | 90 |
| carboxyl groups (%) | 4.8 |
| uretdione groups (%) | 16.0 |
| viscosity (mPa · s/23° C.): | 960 |

The polyisocyanate mixture was dried on glass plates at room temperature and elevated temperature to form clear, hard films. The König pendulum hardness values were 65 sec after drying at room temperature and 85 sec after oven-drying.

The testing of the polyisocyanate mixture according to the invention for stability in storage at room temperature revealed an NCO content of 8.30% and a viscosity of 975 mPa.s after 150 days.

40.1 g dimethyl ethanolamine were added to 1308.2 g of the solution of the polyisocyanate mixture according to the invention in NMP which was then stirred for 5 minutes.

After addition of 1850 g deionized water, a milky blue, slightly transparent aqueous dispersion was formed. The dispersion had a solids content of 39.4%, a viscosity (DIN 4 cup) of 25 sec and an average particle size of the dispersed particles of 112 nm.

EXAMPLE 3 (use)

33 g of a hydroxy-functional polyacrylate resin having a hydroxyl group content of 4% and prepared from 30.6 parts by weight hydroxyethyl methacrylate
17.4 parts by weight methyl methacrylate
40.0 parts by weight butyl acrylate
8.0 parts by weight acrylic acid were adjusted with ammonia solution and water to a pH value of 7.1 so that a 30% solution of the polyacrylate in water was obtained.

After the addition of 0.3 g of a commercially available thickening agent (Acrysol RM 8, a product of Rohm and Haas, Frankfurt) and 0.7 g of a commercially available foam inhibitor (Foamex 1498, a product of Goldschmidt AG, Essen) to the aqueous acrylate solution, 43.4 g of the solution of the polyisocyanate mixture of Example 2 neutralized with 3 g dimethyl ethanolamine were added. The mixture was readily homogenized by simply stirring the mixture.

A film of the mixture applied to a glass plate was tack-free after drying for about 2 h at room temperature and formed a clear, high-gloss, defect-free paint film which, after complete curing, had a König pendulum hardness of 130 sec. After contact with aliphatic hydrocarbons for 1 minute, the film surface remained unchanged. After similar exposure to xylene, methoxypropyl acetate and ethanol, the paint surface underwent slight swelling, but the film was regenerated after evaporation of the solvent.

A film produced in the same way, but without the polyisocyanate solution according to the invention, swelled distinctly on exposure to aliphatic hydrocarbons and was readily soluble in aromatic hydrocarbons or methoxypropyl acetate.

The two-component system containing the polyisocyanate solution according to the invention had a pot life of approximately 4 h.

EXAMPLE 4

100 g of the aqueous polyacrylate solution described in Example 3, to which thickener and foam inhibitor were added as in Example 3, were homogenized with 30.4 g of a polyisocyanate mixture The polyisocyanate mixture was a mixture of

| | |
|---|---|
| 15.2 g | of an isocyanurate polyisocyanate prepared from 1,6-diisocyanatohexane and having an NCO functionality of 3.5, an NCO content of 21.7% and a viscosity at 23° C. of 1,500 mPa · s and |
| 15.2 g | of the polyisocyanate mixture of Example 2 which had previously been neutralized with 1.3 g N,N-dimethyl ethanolamine. |

The NCO/OH equivalent ratio was 1.5:1. A paint film obtained from the formulation was tack-free, glossy and free from defects after drying for 2 hours at room temperature. If the polyacrylate resin was cured solely with the isocyanurate polyisocyanate mentioned, the paint films obtained were distinctly hazy and showed reduced gloss.

After curing at room temperature, the paint film according to the invention had a König hardness of 150 sec. After exposure for 1 minute to the effect of aliphatic and aromatic hydrocarbons and methoxypropyl acetate, the film surface was unchanged. Exposure to the effect of ethanol for the same period produced slight swelling, but the film was regenerated after evaporation of the solvent.

EXAMPLE 5

(catalyzed oligomerization)

1500 g hexamethylene diisocyanate (HDI) were mixed with 60 g dimethyl propionic acid (DMPA) and heated to 55° C. After adding 4.5 g tri-n-butylphosphine and stirring for 4 hours at 60° C., the NCO content of the clear solution had dropped to 37.5%

The reaction was terminated by adding 4.1 g p-toluene sulfonic acid methylester (TSE) and stirring for one hour at 80° C.

Excess HDI was removed from the crude solution by vacuum distillation in a short-path evaporator at 150° C. and 0.05 mbar.

The polyisocyanate mixture containing carboxyl groups was obtained in quantitative yield and had the following characteristics:

| NCO content: | 19.5% |
|---|---|
| Viscosity (23° C.): | 2030 mPas |
| Hazen color index: | 70 |
| Monomer content: | 0.15% unreacted HDI |
| Uretdione groups: | 14.5% |
| Carboxyl groups: | 3.0% |

After 150 days at room temperature, the polyisocyanate mixture containing incorporated carboxyl groups according to the invention had an NCO content of 18.8% and a viscosity of 2110 mPas (23° C.).

After application to a glass plate, the 100% polyisocyanate mixture according to the invention dried after one hour at room temperature in a first case and 30 minutes at 140° C. in a second case to form a clear, crack-free and dust-dry film.

The König pendulum hardness was 60 s for the film dried at room temperature and 85 s for the heat-cured film.

200 g of the polyisocyanate mixture was reacted with 10 g N-dimethylethanol amine, dispersed in 190 g deionized water and stirred until the evolution of gas ceased. A slightly blue aqueous polyurethane-urea dispersion was obtained which had the following properties:

| Solids content: | 46.2% | |
|---|---|---|
| Viscosity (DIN-4 beaker) | 18 s | |
| Average particle size: | 195 mm | |
| Pendulum hardness (König): | Room temp. drying: | 80 s |
| | Oven drying: | 95 s |

EXAMPLE 6

(catalyzed oligomerization)

1100 g hexamethylene diisocyanate (HDI) and 373 g isophoronediisocyanate (IPDI) were mixed with 60 g DMPA and heated to 55° C. After adding 4.5 g tri-n-butylphosphine and stirring for 5 hours at 60° C., the NCO content of the clear solution was reduced to 35.0%.

The reaction was terminated by adding 4.1 g TSE and stirring for one hour at 80° C.

The excess HDI was removed by vacuum distillation as described in Example 5.

The polyisocyanate mixture containing carboxyl groups which was obtained had the following characteristics:

| NCO content: | 18.9% |
|---|---|
| Viscosity (23° C.): | 3180 mPas |
| Hazen color index: | 75 |
| Monomer content: | 0.10% unreacted HDI |
| | 0.12% unreacted IPDI |
| Uretdione groups: | 13.3% |
| Carboxyl groups: | 3.0% |

After 150 days at room temperature, the polyisocyanate mixture containing carboxyl groups according to the invention had an NCO content of 18.2% and a viscosity of 3295 mPas.

After application to a glass plate, the 100% polyisocyanate mixture according to the invention dried in a first case after one hour at room temperature and 30 minutes at 140° C. in a second case to form a clear, crack-free film.

The König pendulum hardness was 80 s for the film dried at room temperature and 98 s for the oven-cured film.

EXAMPLE 7

505.4 g of the starting polyisocyanate based on HDI and described in Example 1 were mixed with 579.0 g of a uretdione/isocyanurate polyisocyanate based on 1-isocyanato-3,3,5-trimethyl-5-isocyanato-methylcyclohexane (IPDI).

The resulting clear solution had an NCO content of 20.2%, a viscosity of 1320 mPas (23° C.) and an average functionality of 2.3.

46.80 g DMPA and
30.60 g NMM (see example 1)

was added to the starting polyisocyanate mixture and stirred at 74° C. until the NCO content of the reaction mixture was reduced to 14.9%.

The polyisocyanate mixture according to the invention had the following characteristic properties:

| Viscosity (mPas 23° C.): | 1795 |
|---|---|
| Hazen color index: | 70 |
| Uretdione groups: | 11 |
| Carboxyl groups: | 0.2% |
| Carboxylate groups: | 1.2% |

Films of the polyisocyanate mixture according to the invention, which were produced and dried as in example 1, were clear and homogeneous.

The König pendulum hardness after 2 hours of air drying was 85 s and after 30 min. oven drying was 108 s. After one minute of exposure to aliphatic and aromatic hydrocarbons and methoxypropylacetate, the film surface of the cured polyisocyanate mixture remained unchanged.

After 150 days at room temperature the polyisocyanate mixture had an NCO content of 14.6% and a viscosity of 1811 mPas (23° C.).

The polyisocyanate mixture could be spontaneously dispersed as described in Example 1.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polyisocyanate mixture which has
   a) an average NCO functionality of 1.5 to 4.0,
   b) a content of (cyclo)aliphatically bound isocyanate groups (calculated as NCO, MW 42) of 2 to 40% by weight,
   c) a content of chemically incorporated carboxyl groups (calculated as COOH, MW 45) of 0.01 to 15% by weight and
   d) a content of (cyclo)aliphatically bound uretdione groups (calculated as $C_2N_2O_2$, MW 84) of 1 to 23% by weight.

2. A process for the production of a polyisocyanate mixture which has
   a) an average NCO functionality of 1.5 to 4.0,
   b) a content of (cyclo)aliphatically bound isocyanate groups (calculated as NCO, MW 42) of 2 to 40% by weight,
   c) a content of chemically incorporated carboxyl groups (calculated as COOH, MW 45) of 0.01 to 15% by weight and
   d) a content of (cyclo)aliphatically bound uretdione groups (calculated as $C_2N_2O_2$, MW 84) of 1 to 23% by weight. which comprises reacting
      a polyisocyanate component comprising at least one diisocyanate having (cyclo)aliphatically bound isocyanate groups, (cyclo)aliphatically bound uretdione groups and a molecular weight of 168 to 1,000 with
      B) a hydroxycarboxylic acid component comprising at least one aliphatic hydroxycarboxylic acid having a molecular weight of 76 to 200
   while maintaining an equivalent ratio of isocyanate groups to hydroxyl groups of 1.05:1 to 80:1 during the reaction.

3. The process of claim 2 which additionally comprises reacting component A) with a positive amount of up to 10% by weight, based on the weight of components A) and B), of a compound containing at least one aliphatically bound hydroxyl group, provided that the equivalent ratio of isocyanate groups to hydroxyl groups of 1.05:1 to 80:1 is maintained.

4. The process of claim 2 which comprises distilling off at least a portion of unreacted polyisocyanate from the polyisocyanate mixture.

5. A process for the production of a polyisocyanate mixture which has
   a) an average NCO functionality of 1.5 to 4.0,
   b) a content of (cyclo)aliphatically bound isocyanate groups (calculated as NCO, MW 42) of 2 to 40% by weight,
   c) a content of chemically incorporated carboxyl groups (calculated as COOH, MW 45) of 0.01 to 15% by weight and
   d) a content of (cyclo)aliphatically bound uretdione groups (calculated as $C_2N_2O_2$, MW 84) of 1 to 23% by weight which comprises
   i) reacting
      A) a polyisocyanate component which is essentially free from uretdione groups and comprises at least one diisocyanate having (cyclo)aliphatically bound isocyanate groups and a molecular weight of 168 to 1,000 with
      B) a hydroxycarboxylic acid component comprising at least one aliphatic hydroxycarboxylic acid having a molecular weight of 76 to 200, while maintaining an equivalent ratio of isocyanate groups to hydroxyl groups of 1.05:1 to 400:1 during the reaction,
   ii) subsequently dimerizing and optionally trimerizing 5 to 60% by weight of the isocyanate groups of the product obtained in i) in the presence of a dimerization catalyst and
   iii) optionally distilling off at least a portion of any unreacted, starting polyisocyanate.

6. The process of claim 5 which additionally comprises reacting component A) with a positive amount of up to 10% by weight, based on the weight of components A) and B), of a compound containing at least one aliphatically bound hydroxyl group, provided that the equivalent ratio of isocyanate groups to hydroxyl groups of 1.05:1 to 400:1 is maintained.

7. A high molecular weight plastic prepared by reacting the polyisocyanate mixture of claim 1 with a reactant containing isocyanate-reactive groups and/or carboxyl-reactive groups.

8. The high molecular weight plastic of claim 7 wherein said polyisocyanate mixture is at least partially neutralized with a tertiary amine.

* * * * *